United States Patent
Erickson et al.

(10) Patent No.: US 9,410,892 B2
(45) Date of Patent: Aug. 9, 2016

(54) NANOSCALE OPTOFLUIDIC DEVICES FOR MOLECULAR DETECTION

(75) Inventors: David Erickson, Ithaca, NY (US); Sudeep Mandal, Lee, MA (US)

(73) Assignee: CORNELL UNIVERSITY, Ithaca, NY (US)

( * ) Notice: Subject to any disclaimer, the term of this patent is extended or adjusted under 35 U.S.C. 154(b) by 1299 days.

(21) Appl. No.: 12/675,370

(22) PCT Filed: Sep. 2, 2008

(86) PCT No.: PCT/US2008/075066
§ 371 (c)(1),
(2), (4) Date: Sep. 14, 2010

(87) PCT Pub. No.: WO2009/029957
PCT Pub. Date: Mar. 5, 2009

(65) Prior Publication Data
US 2011/0039730 A1    Feb. 17, 2011

Related U.S. Application Data

(60) Provisional application No. 60/935,774, filed on Aug. 30, 2007.

(51) Int. Cl.
*G02B 6/12* (2006.01)
*G01N 21/77* (2006.01)
*B82Y 20/00* (2011.01)
*G02B 6/122* (2006.01)
*B01L 3/00* (2006.01)
*G01N 21/78* (2006.01)

(52) U.S. Cl.
CPC ............ *G01N 21/7746* (2013.01); *B82Y 20/00* (2013.01); *G02B 6/12007* (2013.01); *G02B 6/1225* (2013.01); *B01L 3/5027* (2013.01); *G01N 21/774* (2013.01); *G01N 21/78* (2013.01); *G01N 2021/7776* (2013.01); *G01N 2021/7789* (2013.01); *G02B 2006/1213* (2013.01); *G02B 2006/12061* (2013.01); *G02B 2006/12138* (2013.01)

(58) Field of Classification Search
None
See application file for complete search history.

(56) References Cited

U.S. PATENT DOCUMENTS 7,384,797 B1 *   6/2008   Blair ............................ 436/524
2005/0270633 A1 *  12/2005  Herman et al. ............... 359/321

OTHER PUBLICATIONS

Erickson et al (2006 Optics Letters 31:59-61).*
Erickson et al (2005 Anal. Chem. 77: 4000-4007).*
Heilemann et al (2005 JACS 127: 3801-3806).*
Mandal et al (Proc. SPIE 6645, Nanoengineering: Fabrication, Properties, Optics, and Devices IV, 66451J; published Sep. 11, 2007).*

* cited by examiner

*Primary Examiner* — Christopher M Gross
(74) *Attorney, Agent, or Firm* — Perkins Coie LLP

(57) ABSTRACT

An optofluidic architecture for label free, highly parallel, detection of molecular interactions is based on the use of optically resonant devices whose resonant wavelength is shifted due to a local change in refractive index caused by a positive binding event between a surface bound molecule and its solution phase target. These devices have an extremely low limit of detection and are compatible with aqueous environments. The device combines the sensitivity (limit of detection) of nanosensor technology with the parallelity of the microarray type format.

6 Claims, 6 Drawing Sheets

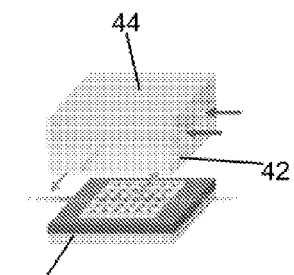
FIG. 6
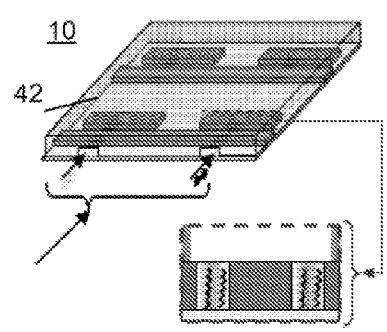
FIG. 7A
FIG. 7B
FIG. 7D
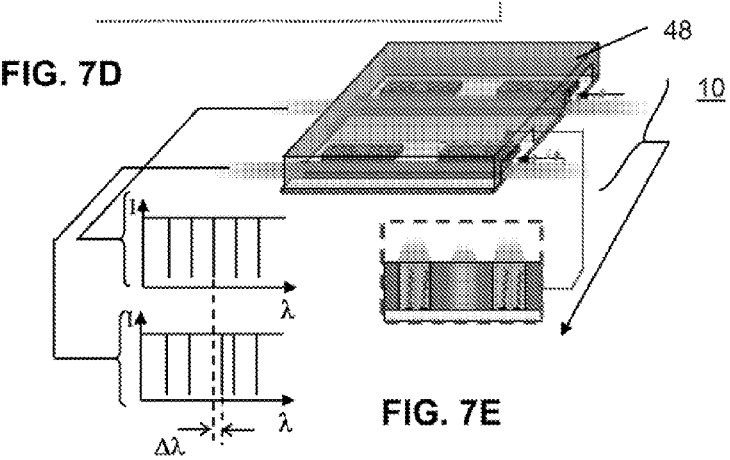
FIG. 7E
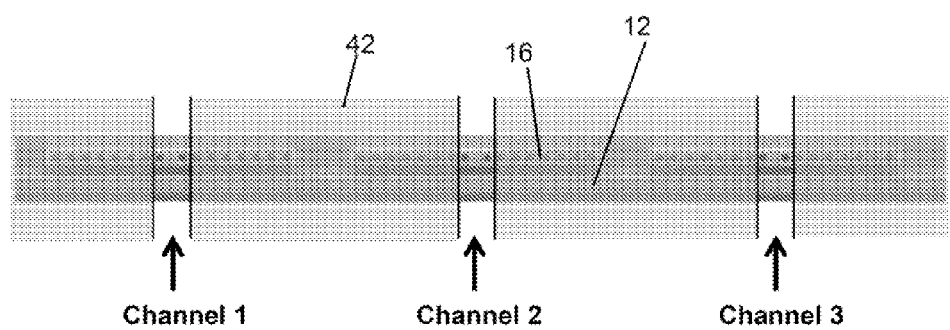
FIG. 7C

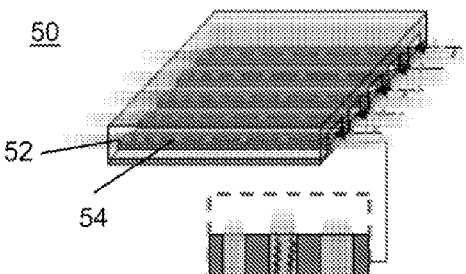
FIG. 8A
FIG. 8B
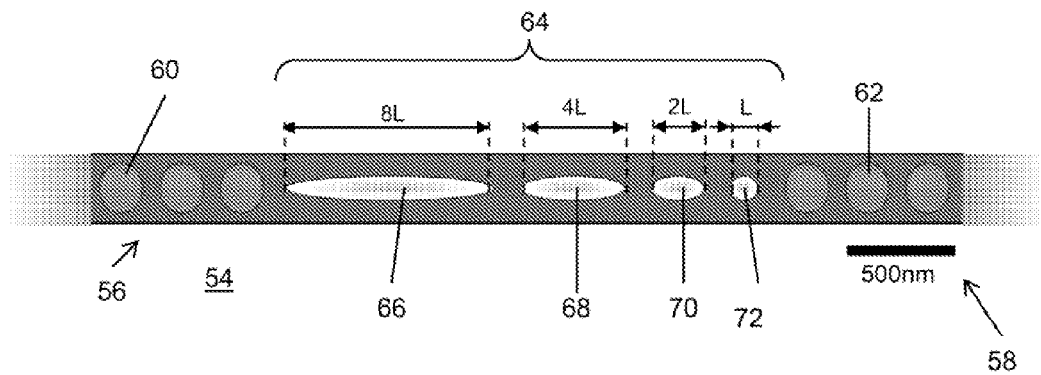
FIG. 9
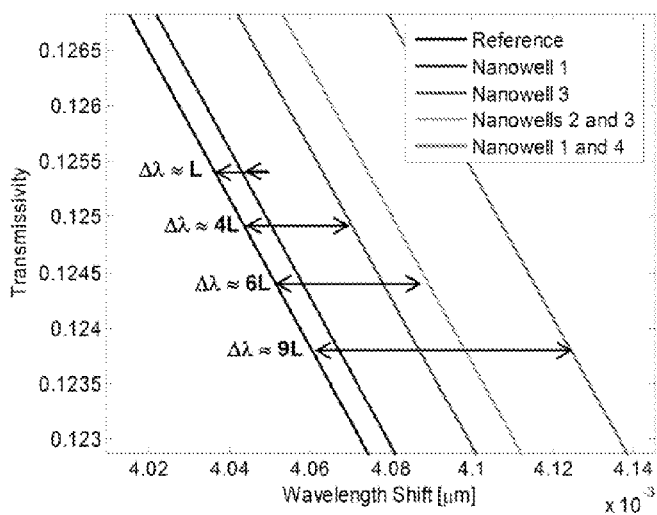
FIG. 10

NANOSCALE OPTOFLUIDIC DEVICES FOR MOLECULAR DETECTION

BACKGROUND OF THE INVENTION

1. Field of the Invention

The present invention relates in general to an optofluidic architecture for label free, highly parallel, detection of molecular interactions. The approach is based on the use of arrays of optically resonant devices, each of which has a resonant wavelength that is shifted due to a local change in refractive index caused by a positive binding event between a surface bound molecule and its solution phase target.

2. Description of the Background Art

Recent interest in the development of new nucleic acid biosensors and high-throughput screening techniques has been largely driven by the potential for associating individual or multiple point polymorphisms with disease states or pharmacological responses, and the need to rapidly diagnose emerging viral threats. To capitalize on these applications, successful next generation sensor platforms should: (1) maximize the total number of biomarker targets against which a sample or multiple samples can be interrogated; (2) minimize the total amount of time and handling required to perform a complete assay; (3) be sufficiently sensitive and specific so as to enable very low, sub-femtogram level detection without the need for target labeling; and (4) minimize the total cost per test.

Existing sensor systems can be separated into traditional and emerging technologies. High-throughput nucleic acid microarrays represent the existing technology which, at present, comes closest to meeting all of the above conditions (addressing (1) and (4) very well and conceivably (2) after incorporation with a suitable microfluidics element, however tending to fail on (3)). To address this failing, emerging nanotechnologies such as nanoparticles, nanowires, nanotubes and nanomechanical or nanophotonic resonators have been developed and represent a quantum leap in terms of sensitivity. The strength of emerging nanosensor technologies is not necessarily that the overall sensitivity is much greater but that the surface area which is probed is much smaller. For example, nanowire devices have achieved very low level detection limits not by increasing the overall sensitivity of the device but by decreasing the binding surface area that is probed. The same is true for nanoparticle based surface plasmon resonance (SPR) and other nanophotonic resonators, and is analogous for nanomechanical resonators. In principal then the challenge in detecting rare solution phase targets is to develop sensors which minimize the resolvable signal multiplied by the probed surface area. In general, nanoparticle based SPR tends to have the smallest probed volume, but tends to have relatively broad adsorption or scattering spectra.

Of the array of optically resonant structures which have been developed into biosensors, planar silicon waveguide resonators and photonic crystals have the next smallest probed surface area. Traditional nanophotonic waveguide resonators are well known to be extremely sensitive to small changes in refractive index and thus have proven themselves to be useful as biological and chemical sensors. Photonic crystal resonator cavities possess very high Q-factors and are very sensitive to changes in the refractive index of their structural elements. They consist of a 1-D or 2-D photonic crystal with a defect in the crystal structure which acts as the resonant cavity. One type of known 2-D photonic crystal microcavity consists of a periodic lattice of cylindrical wells or holes on the order of 100 nm in radius and 200 nm deep in a silicon layer with a central hole defect. Changes in the refractive index in these holes shift the resonant peak which allows them to measure the refractive index of the surrounding liquid medium. In another type of device, a silicon waveguide is flanked on either side by a 1-D or 2-D photonic crystal which causes light corresponding to the photonic bandgap to remain guided in the waveguide. Adsorption of proteins or other biomolecules on the surface of the photonic crystal shifts the bandgap which is detected by observing the transmission spectrum of the waveguide.

While being a novel technique for performing label-free sensing, the extension of these technologies to the extreme parallelity and specificity of the microarray format is complicated by the challenges involved in functionalization of individual sensor elements and two dimensional optical or electrical addressing of reaction sites with sub-micrometer spacing. More specifically, inherent in the nature of such devices is the existence of a band gap surrounding the resonant peak which prohibits optical transmission over a large range of wavelengths (typically on the order of 100 nm). This generally negates the possibility of multiplexing different reaction sites along a single optical structure, thereby prohibiting two dimensional multiplexing.

SUMMARY OF THE INVENTION

The present invention comprises a device and method of using the same that are particularly useful for nucleic acid biosensing and provide the sensitivity of known nanoscale technologies, while overcoming the aforementioned bandgap problems that have until now prevented multiplexing of different reaction sites. To accomplish this, the invention preferably employs an array, referred to as a nanoscale optofluidic sensor array (NOSA), of one dimensional (1-D) waveguide sensors, each of which is fabricated with one or more unique optical resonator sensors. The optical resonator sensors, which are preferably formed from photonic crystals, each has a resonant wavelength that is altered when a positive binding event or other index of refraction altering reaction occurs in an optical cavity of the resonator sensor. In each embodiment of the invention, each resonator sensor is designed to alter an incident light beam in such a manner that the presence of a binding or other interaction at any of the sensors can be detected through analysis of the wavelength spectrum of the output light beam from each 1-D waveguide sensor.

In a first embodiment of the invention, referred to as the side resonator embodiment, the resonator sensors lie to the side of a waveguide that is excited by an incident optical light beam, such as from a low power laser. In this configuration, light at the resonant wavelength, which is initially traveling in the waveguide, is evanescently coupled into the resonator sensor. This results in a dip in the output spectrum at that given wavelength. Because the resonator sensors lie to the side of the waveguide, the bandgap does not interfere with the light transmission outside of that which lies in the resonant peak. As a result, multiplexing along a single waveguide is obtained simply by placing a large number of side resonator sensors along the waveguide, each of which has a slightly different resonant wavelength. The change in the resonant wavelength is preferably obtained by altering the length of the optical cavity of each side resonator sensor.

In a second embodiment of the invention referred to as the inline resonator embodiment, the NOSA sensor consists of a waveguide resonator sensor with an extended cavity containing a series of differently sized reaction sites, each of which may be formed in a nanowell. For example, a first reaction site or well has a first length L, a second reaction site or well has a length 2L, a third reaction site or well has a length 4L and a fourth reaction site or well has a length 8L. A change in refractive index in the first reaction site or well results in a corresponding shift of the resonant wavelength of the resonator sensor because the increase in refractive index effectively increases the overall optical length of the cavity. When a similar refractive index change is induced in the second and third reaction sites or wells (which are 2 and 4 times as long, respectively), shifts of approximately twice and four times that obtained for the first reaction site or well are obtained. This result extends to the case when a refractive index change is observed in multiple reaction sites or wells. For example, a change in reaction sites or wells two and three results in a shift of approximately 6 times that observed for the first reaction site or well. This unique relationship allows one to design the sensor structure such that a positive binding event in any reaction site or well or combination of reaction sites or wells causes a unique spectral shift. For example, positive binding events in reaction sites or wells 1, 2 and 3 would result in a shift of 1+2+4=7 times that of the base shift whereas a reaction in reaction sites or wells 1 and 4 would cause a shift of 1+8=9 times.

In the operation of both embodiments of the invention, a two stage nanofluidic approach is employed which enables unique probe functionalization and target addressing of each reaction site. In a first, functionalization stage, soft lithography nanofluidics are aligned and placed perpendicular to the waveguide sensors. In this arrangement the fluidics are used to independently immobilize different oligonucleotide probes in each of the reaction sites along the length of each NOSA. After functionalization, the initial fluidics are removed and a second, screening stage is executed. The screening fluidics are applied perpendicular to the original orientation. Facile exchange in this manner is preferably made possible through the use of elastomeric (PDMS) based fluidics which provide the required conformable and reversible sealing to the photonic structures. The screening nanofluidics preferably consist of one nanochannel per photonic test waveguide and are used to deliver the samples directly into the reaction sites. For target delivery, electrokinetic transport is preferably employed. This facilitates transport in the nanochannels since the front velocity is largely independent of channel size but more importantly it provides a simple technique by which non-specific binding can be reduced and reaction specificity ensured to the single nucleotide level.

The NOSA of the present invention provides the following advantages over known devices: (1) has attogram level detection sensitivity without the need for target labeling; (2) enables independent functionalization of individual nano-sensing sites in one implementation with sub-micron spacing; (3) ensures each solution phase nucleic acid target has multiple opportunities to hybridize with its surface immobilized complement; (4) allows for two dimensional multiplexing at reaction densities at least an order of magnitude greater than standard microarrays; and (5) enforces reaction specificity through a unique electrokinetic stringency technique.

The use of nanoscale fluidics not only enables individual reaction site addressability but also provides spatial confinement of the targets near the reaction site, increasing the number of target:probe collisions and ensuring that each molecule has an opportunity to become hybridized. In addition, the use of an electrokinetic transport mechanism increases the throughput capabilities (since the flow velocity is largely independent of channel size).

BRIEF DESCRIPTION OF THE DRAWINGS

The foregoing and other features and advantages of the invention are described in detail below, in conjunction with the accompanying drawings, which are briefly described as follows.

FIG. 6 is a schematic illustration of multi-layer soft-lithography coupling with nanophotonics which is employed to fluidically address and tune photonic structures at the nanoscale in the embodiments of the present invention.

FIGS. 7A-7E are graphical illustrations showing two different operational stages of a NOSA constructed in accordance with the first preferred embodiment of the present invention. FIGS. 7A and the close up of 7B show a functionalization stage in which oligonucleotide probe immobilization is conducted in the optical cavities of side resonator sensors by aligning PDMS fluidics opposite the direction of the bus waveguides. FIG. 7C is an illustration of one bus waveguide section of the NOSA of FIG. 1A showing 3 of the side resonator sensors with graphically superimposed boxes which illustrate functionalization channel location. FIGS. 7D and the close up of 7E illustrate a screening stage in which delivery fluidics are aligned and sealed and one sample is introduced per resonator sensor.

FIGS. 8A, 8B and 9 are graphical illustrations of a second embodiment of the present invention comprising a NOSA which employs a single optical resonator sensor formed in line with each bus waveguide of the array. The resonator sensor employs a cavity design which comprises multiple reaction sites or wells of increasing size.

FIG. 10 is a graph showing the shift in resonant peak due to a change in refractive index of 0.001 in the 4 different sized reaction sites of the resonator sensor of FIG. 9.

DETAILED DESCRIPTION OF THE INVENTION

With reference now to a more detailed description of a number of embodiments of the present invention and variations thereon, the heart of the invention and the method of using the same is referred to as a nanoscale optofluidic sensor array (NOSA). The NOSA is preferably employed for nucleic acid biosensing, but can be used to detect any molecular interaction that results in a shift of the resonant wavelength of an optical resonator sensor. Broadly speaking, the technique relies on shrinking the nanofluidic system down to the same scale as that of the wavelength of light and using a unique nanophotonic resonator sensor to both gain access to the evanescent optical field and provide attoliter scale spatial localization of the reaction site. Two specific embodiments of the NOSA array are disclosed herein, although it will be understood that the invention is not limited to these and other implementations could be devised. As will be discussed below, both embodiments have the same basic operational architecture but a slightly different detector design.

The use of nanoscale fluidics not only enables individual nanowell addressability, but also provides spatial confinement of the targets near the reaction site, increasing the number of target:probe collisions and ensuring that each molecule has an opportunity to become hybridized. As will also be outlined in greater detail below, the use of an electrokinetic transport mechanism not only increases the throughput capabilities (since the flow velocity is largely independent of channel size) it also enables use of a recently developed technique for electrokinetic based specificity which has proven successful down to the single nucleotide level. The two stage nanofluidic approach enables unique probe functionalization and target addressing of each nanowell.

Figure 1A:
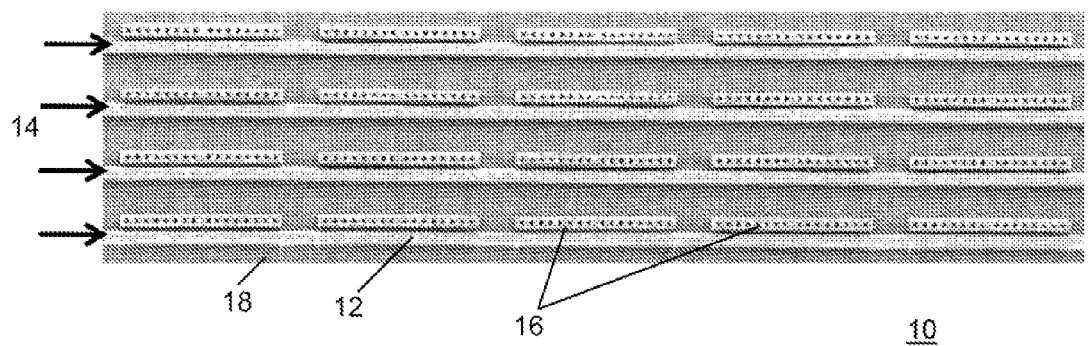
FIG. 1A is an illustration of a 4×5 nanoscale optofluidic sensor array (NOSA) constructed in accordance with a first preferred embodiment of the present invention which includes a group of 4 bus waveguides, each having a group of 5 resonator sensors disclosed alongside the waveguide in series.
Figure 1B:
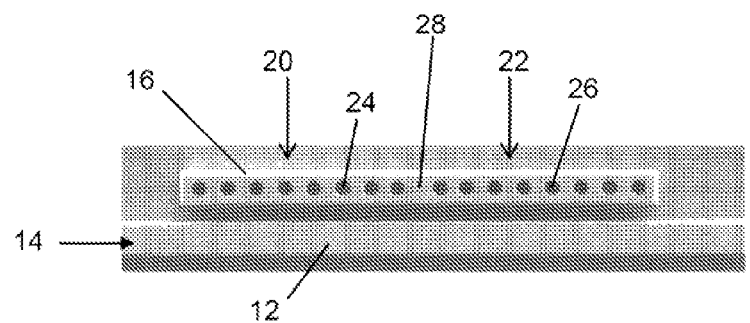
FIG. 1B is a close up showing the detail of one of the side resonator sensors.

The first embodiment of the invention is referred to as the side resonator embodiment and is illustrated in FIGS. 1A and 1B. With reference first to FIG. 1A, a 4×5 NOSA 10 is shown which includes a group of 4 parallel bus waveguides 12 for receiving incident optical excitation beams 14. In this embodiment, a series of 5 nanophotonic optical resonator sensors 16 lie to the side of and are evenly spaced from each of the waveguides 12. As an example, 4 samples can be independently tested against the 5 required probe sites (one for each serotype and a negative control) using the NOSA 10. The NOSA 10 is preferably formed using silicon on insulator (SOI) technology where the waveguides 12 and resonator sensors 16 are formed from silicon on a silicon dioxide wafer or substrate 18.

With reference to the close-up view of FIG. 1B, each of the resonator sensors 16 is formed of first and second 1-D photonic crystals (PCs) 20 and 22, each of which is formed of first and second groups of spaced nanowells or holes 24 and 26, respectively. The nanowells 24 and 26 have a different dielectric permittivity than that of the surrounding silicon. The resulting periodic variation in dielectric permittivity results in a band of wavelengths in the bandgap of the PCs 20 and 22 which are not allowed to propagate. In this manner, the PCs 20 and 22 each act as a mirror to these wavelengths. Each resonator sensor 16 is easily tunable by adjusting the length of a central defect cavity 28, which acts both as a resonator and a reaction site or sensing element. Light couples evanescently from the adjacent waveguide 12 into the cavity mode of the resonator sensor 16. The NOSA 10 can be easily multiplexed by adding more resonator sensors along the same waveguide, since each resonator sensor generates a characteristic signature in the output spectrum.

Figure 2:
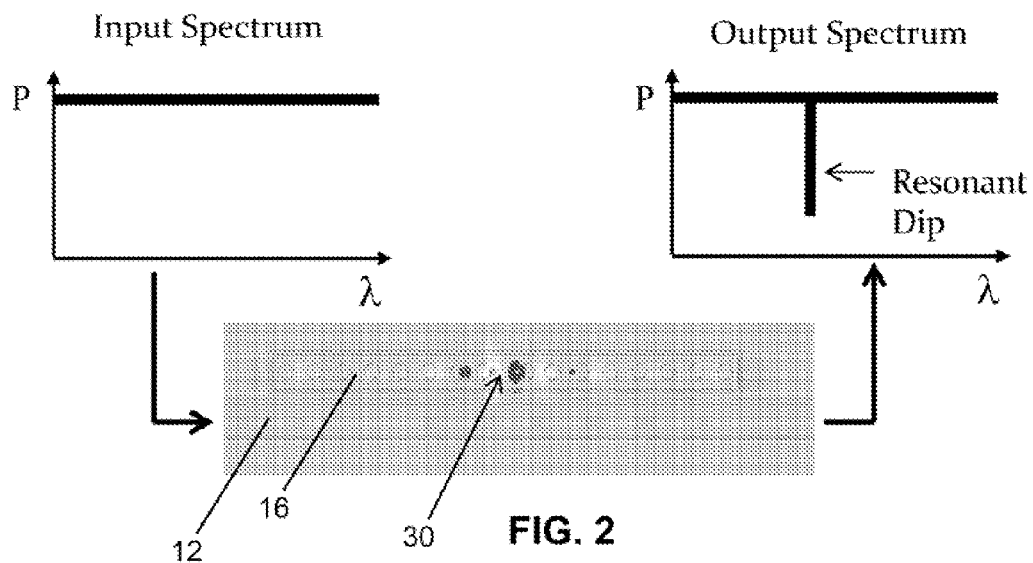
FIG. 2 is a graphical illustration of the working principle of the NOSA of FIG. 1A in which one of the side resonator sensors is shown with finite different time domain (FDTD) simulations showing the light intensity pattern at resonance which is induced in the sensor's resonator cavity by evanescent coupling of an incident light beam passing through the adjacent bus waveguide. The resulting dip in the output spectrum of the light beam passing through the adjacent bus waveguide is also depicted.

In the configuration employed in the side resonator embodiment, light at the resonant wavelength of one of the resonator sensors 16, which is initially traveling in the waveguide 12, is evanescently coupled into that one of the resonator sensors 16. The result is a dip in the output spectrum at that given wavelength. This operating principle is graphically depicted in FIG. 2 in which one of the side resonator sensors 16 is shown with FDTD simulations showing a light intensity pattern 30 at resonance which is induced in the resonator cavity 28 by evanescent coupling of the incident light beam 14 passing through the adjacent bus waveguide 12. This resonance results in a dip in the output power spectrum of the light beam passing out of the waveguide 12 as illustrated.

Figure 3:
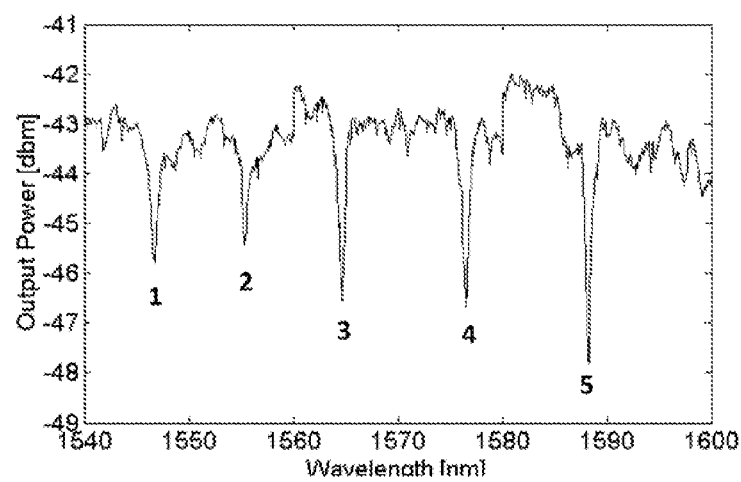
FIG. 3 is a graph of experimentally obtained resonant dips in the output spectrum of one of the bus waveguides of the NOSA of FIG. 1A.

Evanescent coupling ensures that the resonator sensor bandgap does not interfere with the light transmission through the waveguide 12 because the resonator sensors 16 lie to the side of the waveguides 12. As a result, multiplexing along any single one of the waveguides 12 is obtained simply by placing a large number of the side resonator sensors 16 along the waveguide 12, each of which has a slightly different resonant wavelength. The graph of FIG. 3 shows experimentally obtained resonant dips in the output spectrum of one of the bus waveguides 12 of the NOSA 10 of FIG. 1A. Each of the 5 dips corresponds to, and thus acts as a signature for, one of the 5 adjacent resonator sensors 16. Although the embodiment of FIG. 1A employs 5 of the resonator sensors 16 for each of the waveguides 12, it should be understood that any suitable number of resonator sensors can be employed. Based on the results of the experiments conducted on the side resonator embodiment of the invention, it is expected to be able to multiplex at least 25 resonator sensors along a single waveguide and still be able to distinguish the characteristic signatures of each resonator sensor.

Figure 4:
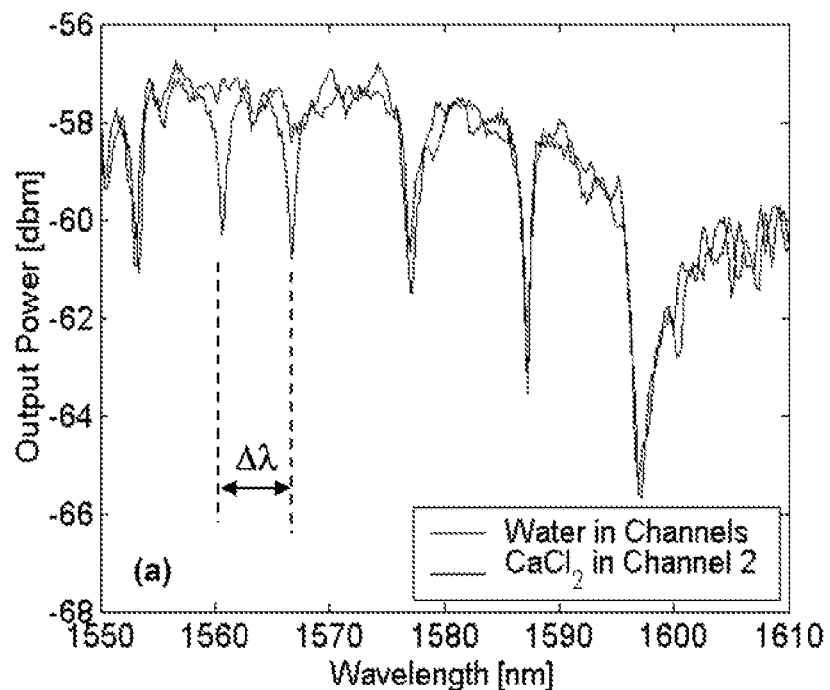
FIG. 4 is a graph showing the change in resonant dip location in response to change in local refractive index. The initial graph shows the initial 5 resonator sensor system of the NOSA of FIG. 1A each addressed with a separate microchannel filled with water (n=1.33). The second graph with the section for channel 2 shifted to the right shows a red shift in the dip induced by the second resonator sensor in response to the introduction of a ~1M $CaCl_2$ solution.
Figure 5:
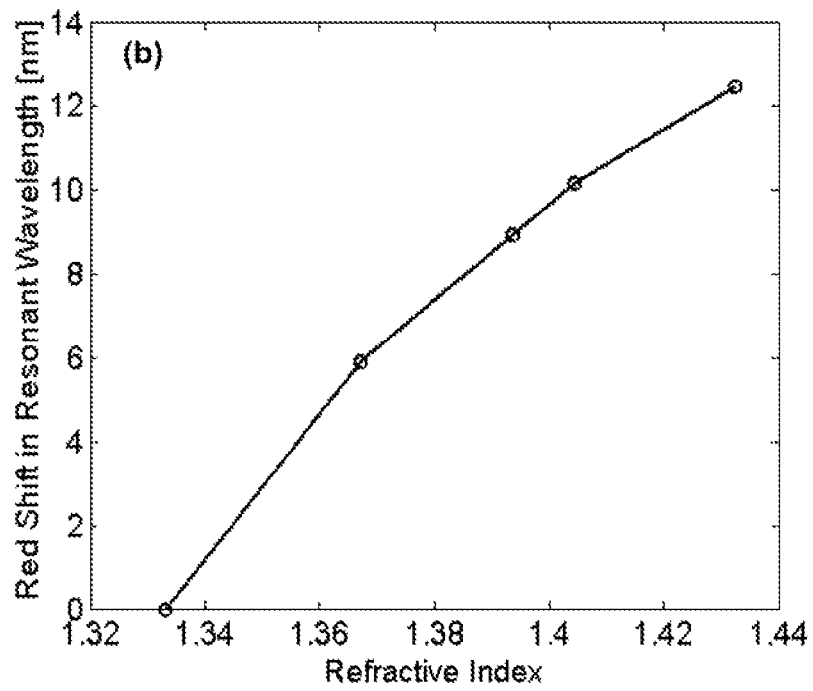
FIG. 5 is a graph depicting sensitivity experiments on the NOSA of FIG. 1A showing the shift in resonant dip as a function of local refractive index.

When a complementary target is introduced to one of the resonator sensors 16, molecular binding increases the mass of organics in the cavity 28 and thus the local refractive index is also increased. The result is a red shift of the resonant dip similar to that shown in the graph of FIG. 4, which shows the change in resonant dip location in response to change in local refractive index. The initial graph shows the initial 5 resonator sensor system of the NOSA 10 of FIG. 1A, where each resonator sensor is addressed with a separate microchannel filled with water (n=1.33). The second graph with the section for channel 2 shifted to the right shows red shift in the dip induced by the second resonator sensor in response to the introduction of a ~1M $CaCl_2$ solution. FIG. 5 is a graph depicting sensitivity experiments on the NOSA of FIG. 1A showing the shift in resonant dip as a function of local refractive index. These experiments confirm the ability of the NOSA 10 to detect and identify the location of molecular interactions that occur at any of the resonator sensors 16.

FIG. 6 is a schematic illustration of multi-layer soft-lithography coupling with nanophotonics which is employed to fluidically address and tune photonic structures at the nanoscale in the embodiments of the present invention. As shown, a NOSA constructed in accordance with the preferred embodiments includes three main structural components: a photonics layer 40, a fluidics layer 42 and a valve layer 44. The photonics layer 40 is what is shown in FIG. 1A, for example, while the flow and valve layers are employed to carry out two operational stages of the NOSA: functionalization of the reaction sites and screening of the sites to deliver samples thereto for binding detections.

FIGS. 7A-7E are graphical illustrations showing the two different operational stages of the first preferred embodiment of the present invention. FIGS. 7A and the close up of 7B show a functionalization stage in which oligonucleotide probe immobilization is conducted in the optical cavities of the side resonator sensors 16 by aligning PDMS fluidics 42 opposite to the direction of the bus waveguides 12. FIG. 7C is an illustration of one section of the NOSA 10 of FIG. 1A showing the bus waveguide 12 and 3 of the side resonator sensors 16 with the PDMS fluidics 42 graphically shown as defining the location of first, second and third functionalization channels. FIGS. 7D and the close up of 7E illustrate a screening stage in which delivery fluidics are aligned and sealed and one sample is introduced per resonator sensor 16.

During the first functionalization stage, probe immobilization is conducted by first activating the surface of the resonator cavities with a dendrimer chemistry, then aligning the PDMS nanofluidics 42 perpendicular to the direction of the waveguides 12 and finally flowing through a solution of the EDC coupling agent and oligonucleotide probes. This allows one to spatially localize the binding sites to the optical cavity of the side resonator sensors 16. Using this technique, each of the resonator sensors 16 along the length of each bus waveguide 12 is functionalized with a different probe.

More specifically, the dendrimer chemistry involves the use of either piranha etch or plasma oxidation to generate surface silanol groups, to which the amine-terminated silane APTMS (aminopropyltrimethoxysilane) are coupled. Carboxylic acid terminated dendrimers (64 functionalities per dendrimer) are then covalently linked to amine-functionalized surfaces via water soluble carbodiimide chemistry to increase the surface probe density. The functionalization fluidics 42 are then aligned with the resonator sensors 16 and attached to the NOSA 10. Amine-terminated capture DNA with sequences specific to the serotypes of interest is then flown over the resonator sensors 16, bonding with the open groups on the dendrimers. In one experiment, this was characterized by using TAMRA tagged probes and equating the relative intensity of the florescence signal to the surface probe density. In the actual detection experiments, a 0.2% PVP (polyvinylpyrrolidone) surface passivation step was also used in an effort to limit non-specific DNA adsorption.

After functionalization, the original fluidics 42 are removed, screening fluidics 48 are applied and the sample is introduced as illustrated in FIGS. 7D and 7E. Facile exchange in this manner is only possible through the use of elastomeric (e.g. PDMS) based fluidics which provide the required conformable and reversible sealing to the photonic structures. The screening nanofluidics 48 preferably consist of one nanochannel per photonic test waveguide and are used to deliver the samples directly into the nanowell sites. A recently developed, unique architecture for integrating active nanofluidic elements with silicon-on-insulator photonic crystals is preferably employed (see Erickson, D., T. Rockwood, T. Emery, A. Scherer, and D. Psaltis, *Nanofluidic tuning of photonic crystal circuits*. Optics Letters, 2006. 31(1): p. 59-61). This architecture enables fluidic addressability of individual sub-wavelength scale photonic elements (volume of 5 attoliters). The ability to address volumes this small within a photonic structure is key to achieving the mass sensitivity required.

For target delivery, electrokinetic transport is preferably employed. This facilitates transport in the nanochannels since the front velocity is largely independent of channel size but more importantly it provides a simple technique by which non-specific binding can be reduced and reaction specificity ensured to the single nucleotide level. Applying an electrokinetic driving potential allows for precise manipulation of the thermal (through Joule heating), shear (through electroosmotic flow) and electrical (through electrophoresis) forces enabling the SNP to be discriminated. In another recent work (Erickson, D., X. Z. Liu, R. Venditti, D. Q. Li, and U. J. Krull, *Electrokinetically based approach for single-nucleotide polymorphism discrimination using a microfluidic device*. Analytical Chemistry, 2005. 77(13): p. 4000-4007) it has been demonstrated that through proper control over the shear, electrophoretic and thermal energies within the electrical double layer (a region extending ~50 nm into the liquid environment from the surface) one can control reaction specificity down to the single nucleotide level. The technique relies on applying sufficient local energy to the system such that DNA hybrids that differ from the target strand by a single base pair are pulled apart, while perfectly matched hybrids remain bound. Experiments have confirmed that nearly perfect discrimination is obtained with a very strong signal obtained at the complementary probe site and no appreciable signal obtained at the probes with a single nucleotide difference. Kinetic measurements should also be able to be made with this arrangement.

FIGS. 8A and 8B illustrate a second embodiment of the invention referred to herein as the inline resonator embodiment. In this embodiment, a NOSA 50 is provided, which as in the first embodiment, comprises a plurality of parallel waveguides 52. However, the inline resonator embodiment differs from the side resonator embodiment in that a single optical resonator sensor 54 is formed in each of the waveguides 52. The optical resonator sensor 54 includes first and second photonic crystals 56 and 58, in each of which is formed of a plurality of nanowells 60 and 62, respectively. As illustrated in FIG. 9, the NOSA 50 employs a unique optical cavity 64 which contains a plurality of reaction sites or wells 66, 68, 70 and 72 of increasing size. When a change in refractive index in one of the reaction sites or wells is observed, the effective optical length of the cavity 64 is increased along with the wavelength of the resonant modes. In this embodiment, each successive reaction site or well is twice the length of the previous reaction site or well. Because of this relationship, the amount that the resonant wavelength peak shifts can be uniquely related to the combination of the reaction sites or wells 66-72 in which a binding reaction has occurred.

To illustrate the operating principle of this embodiment and to quantitatively estimate device sensitivity, a series of 2-D finite different time domain (FDTD) simulations were conducted. The simulation domain consisted of a 470 nm wide silicon waveguide (n=3.5) excited over a range of wavelengths. The nanowells 60 and 62, which define the resonator band gap, were assigned the properties of silica (n=1.5) and the reaction wells were assumed to have an initial refractive index of 1.33 (consistent with that of an aqueous solution). The reaction nanowells in the simulation were all 250 nm wide and L from FIG. 9 was 200 nm. The extended cavity resulted in multiple resonant peaks within the bandgap. Though the cavity is multimode, as long as the peaks are sufficiently well separated, they do not pose an inherent problem.

FIG. 10 is a graph showing the shift in resonant peak due to a change in refractive index of 0.001 in the 4 different sized reaction sites or wells of the resonator sensor of FIG. 9. As shown, a change in refractive index in any of the reaction sites or wells increases the optical length of the cavity and thus the wavelength of the resonant peak. Since the reaction site or well sizes are selected such that each is double the size of its predecessor, a refractive index change in any combination of the reaction sites or wells causes a shift to a unique location. More specifically, a change in refractive index of $\Delta n=10^{-3}$ in the first reaction site or well results in a shift of approximately 0.007 nm. The reason for this is that the increase in refractive index effectively increases the overall optical length of the cavity. When a similar refractive index change is induced in the second and third reaction sites or wells (which are 2 and 4 times as long), shifts of approximately twice (not shown) and four times (shown) that obtained for the first reaction site or well were obtained. This result extends to the case when a refractive index change is observed in multiple reaction sites or wells. For example, a change in reaction sites or wells two and three results in a shift of approximately 6 times that observed for the first reaction site or well. This unique relationship allows one to design the sensor structure such that a positive binding event in any reaction site or well or combination of reaction sites or wells causes a unique spectral shift. For example positive binding events in reaction sites or wells 1, 2 and 3 would result in a shift of 1+2+4=7 times that of the base shift whereas a reaction in reaction sites or wells 1 and 4 would cause a shift of 1+8=9 times. Note that while these simulations were conducted for $\Delta n=10^{-3}$, further simulations suggest detection levels on the order of $\Delta n=10^{-4}$ should be possible at the resolution limit of the existing tunable infrared laser. Although this embodiment of the invention provides the ability to multiplex detections, the first, side resonator embodiment can generate more detections per waveguide because the side resonator configuration does not affect the bandgap of the incident light beam as does the inline embodiment.

Figure 11:
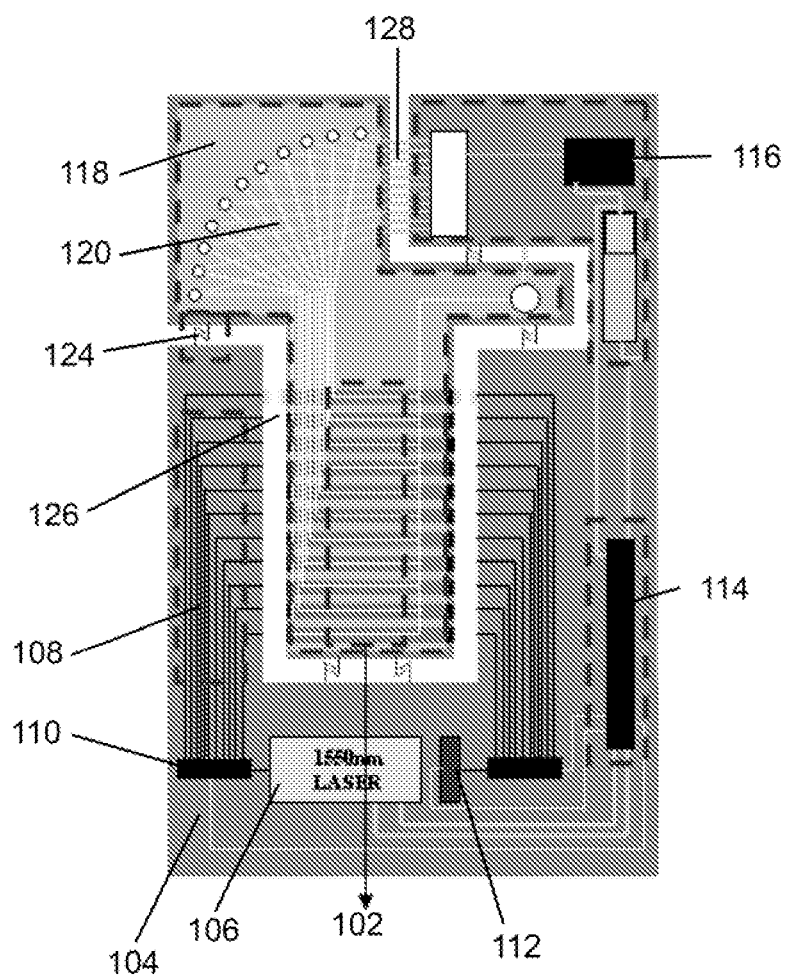
FIG. 11 illustrates an optofluidic detection system which employs a NOSA in accordance with the embodiments of the present invention.

FIG. 11 illustrates an optofluidic detection system 100 which employs a NOSA 102 that is constructed in accordance with any of the embodiments of the present invention or variations thereon. The system 100 includes a reusable structure 104 which performs all signal processing, communications, etc. and includes a low power 1550 nm laser 106, silicon-on-insulator (SOI) waveguides 108, optical switches 110, optical power sensor 112, signal processing and control circuitry 114 and a low power system 116 for electrokinetic sample transport. The optical switches 110 allow the light from the laser 106 to be selectively directed to each of the waveguides 108 which are interfaced to each of the waveguides in the NOSA 102. It should be understood, however, that multiple lasers could be employed, if desired, to eliminate the need for the optical switches 110.

The system 100 also includes a disposable optofluidic cartridge 118 which contains micro/nano-fluidics channels 120, nanoneedles for sample collection and the NOSA 102. MEMS latches 124 are provided to couple the reusable structure 104 and the disposable optofluidic cartridge 118. In addition, optical interconnects 126 and chip-chip electrical interconnects 128 are provided to interconnect the various components of the system 100.

The fabrication procedure for a NOSA constructed in accordance with any embodiments of the invention employs conventional E-beam lithographic and PDMS casting techniques. As already discussed in conjunction with FIG. 6, each NOSA structure includes 3 main structural components: a photonics layer structure, a nanofluidics layer structure and a valve layer structure. The photonics structure is fabricated by defining a pattern on an SOI wafer with an E-beam, followed by developing of the resist and dry etching to define the photonics structure. Similarly, the nanofluidics structure is formed in the same manner, but also includes additional photolithography to add microfluidics. Casting and curing of the PDMS is then carried out. Finally, photolithography is also employed to define valves and then the PDMS is cast, cured and removed.

In summary, the NOSA sensor platform described herein represents a substantial improvement in the state of the art. Calculations suggest that the platform has the potential for as much as a 100 fold increase in the mass sensitivity over the state of the art. Functionalization of the surface should not reduce sensitivity since the shift is based on changes in $\Delta n$ (i.e. surface functionalization will represent a shift in the base state, but it is not significantly expected to reduce overall sensitivity). One of the major thrusts in biosensor design is in decreasing the mass limit of detection (LOD) to enable earlier pathogen detection or to detect more obscure biomarkers. A refractive index change of $\Delta n_{eff}=0.009$ has been reported for an oligonucleotide surface density of 112 ng/cm$^2$ probed using an evanescent technique. Translating this to the cavity surface area in the NOSA and a measured sensitivity of ~150 nm/RIU, this suggests that 1 attogram of adsorbed mass will result in a wavelength shift of $\Delta\lambda=0.005$ nm, which is well above the resolution of the laser ($\Delta\lambda=10^{-4}$ nm) used in the experiments on the preferred embodiments. This places the LOD well below most resolution liquid phase nanosensor platforms).

In initial nucleic acid detection experiments, a 4 resonator NOSA sensor was functionalized with probes specific to (R1) Dengue Virus serotype 3, (R2) a control sequence and (R3) Dengue Virus serotype 1 (the fourth resonator sensor was used as a refractive index calibrator). After removal of the functionalization fluidics, a solution containing serotype 3 targets in 4×SSC buffer, containing formamide and ficoll was introduced. After a 15 minute hybridization time and buffer wash, a shift of approximately 0.35 nm was measured at the complimentary site compared with approximately 0.05 nm at the control and 0.15 nm at the non-complementary serotype. This result confirms that the embodiments of the invention do work as expected and readily detected the larger wavelength shift imparted by the complementary site where the binding of the probe and target sample was expected to occur.

Although the invention has been disclosed in terms of a number of preferred embodiments and variations thereon it will be understood that numerous other variations and modifications could be made thereto without departing from the scope of the invention as defined in the following claims. For example, although the preferred embodiments are particularly useful for detecting binding of biological probes and targets, the invention can be used to detect any type of optically detectable molecular interaction or reaction that changes the resonant wavelength of the resonant sensors. Further, although variation of the resonant wavelength of the sensors through variation of the index of refraction, which induces a change in the effective cavity length of the sensor, is preferred, other techniques, such as temperature changes, could be employed to change the resonant wavelength through actual change of the optical cavity length. In addition, while the use of different cavity lengths is preferred in the embodiments of the invention, different materials having different indexes of refraction to begin with could be employed to provide each reaction site with a different, detectable signature.

The invention claimed is:

1. An optofluidic device for optical sensing, comprising:
    a photonics structure including a wafer on which photonics components are formed to provide optical sensing and detection in the optofluidic device, the photonics structure includes:
    (1) a plurality of one-dimensional optical resonator sensor arrays, each one-dimensional optical resonator sensor array includes optical resonator sensors spaced at different locations along a line so that the one-dimensional optical resonator sensor arrays form a two-dimensional arrays of optical resonator sensors, each optical resonator sensor configured to include a first group of photonic crystals forming a first resonator reflector and a second group of photonic crystals forming a second resonator reflector to effectuate an optical resonator exhibiting a unique optical resonant wavelength different from other optical resonant wavelengths in other optical resonator sensors in the same one-dimensional optical resonator sensor array and one or more reaction wells located between the first and second resonator reflectors of the optical resonator, each reaction well configured to be functionalized with a molecular probe for binding with a target sample to effectuate a detectable shift in a corresponding unique optical resonant wavelength for an optical resonator sensor, (2) a plurality of optical waveguides carrying and guiding probe light and optically coupled to the one-dimensional optical resonator sensor arrays, respectively, one optical waveguide per one-dimensional optical resonator sensor array, wherein each optical waveguide couples the guided probe light into each of the optical resonator sensors in a corresponding one-dimensional optical resonator sensor array and couples light from the optical resonator sensors to produce an output beam that contains information at different unique optical resonant wavelengths indicating one or more samples attached to molecular probes in the reaction wells in the same one-dimensional optical resonator sensor array; and (3) an optical detector module coupled to the optical waveguides to receive an output beam from each optical waveguide having optical signals at different unique optical resonant wavelengths associated with different optical resonator sensors in the same one-dimensional optical resonator sensor array to measure a shift in each of the different unique optical resonant wavelengths;

a nanofluidics structure coupled to the photonics structure and including fluidic channels coupled to reaction wells in the optical resonator sensors to guide fluidic flows to or from the reaction wells for optical sensing and detection in the optofluidic device; and a fluidic valve structure including fluidic valves coupled to the fluidic channels of the nanofluidics structure to manage the fluidic flows in the fluidic channels for optical sensing and detection in the optofluidic device, wherein the nanofluidics structure is positioned between the photonics structure and the fluidic valve structure such that the fluidic valve structure, the nanofluidics structure, and the photonics structure form a three-layer stack.

2. The optofluidic device of claim 1, comprising:
a light source that produces the probe light; and
an optical switch coupled between the optical waveguides and the light source to switch light from the light source into the optical waveguides for optical sensing.

3. The optofluidic device as in claim 1, wherein:
the nanofluidics structure includes an electrokinetic transport system for transporting fluidic flows though the fluidic channels to the reaction wells for optical sensing and detection in the optofluidic device.

4. The optofluidic device of claim 1, wherein the photonics structure includes a second one dimensional detector array separated from the first optical resonator sensors to include optical resonator sensors located at different locations in the second one dimensional detector array and reaction sites spatially distributed in different optical resonator sensors in the second one dimensional detector array, and a second optical waveguide positioned to be optically coupled to each of the optical resonator sensors of the second one dimensional detector array, and wherein the fluidic channels in the nanofluidics structure include a second set of fluidic channels that are coupled to the reaction sites in the optical resonator sensors in the second one dimensional detector array to deliver fluidic samples to the reaction sites.

5. The optofluidic device of claim 1, wherein:
each optical waveguide is placed outside and adjacent to a respective one-dimensional optical resonator sensor array so that each optical resonator sensor optically evanescently coupled to the optical waveguide.

6. The optofluidic device of claim 1, wherein:
each optical resonator sensor in each one-dimensional optical resonator sensor array has a different optically resonant cavity length from other optical resonator sensors in the same one-dimensional optical resonator sensor array so that different optical resonator sensors in the one-dimensional optical resonator sensor array have different optically resonant wavelengths.

* * * * *